US00PP25006P3

(12) United States Plant Patent
De Wit et al.

(10) Patent No.: US PP25,006 P3
(45) Date of Patent: Oct. 28, 2014

(54) APPLE TREE NAMED 'IMARA'

(50) Latin Name: ***Malus domestica* Borkh.**
Varietal Denomination: Imara

(71) Applicant: Better3fruit, N.V., Heverlee (BE)

(72) Inventors: Inge De Wit, Lovenjoel (BE); Hendrik Eyssen, Holsbeek (BE); Johan Keulemans, Korbeek-Lo (BE); Johan Nicolaï, Sint-Truiden (BE); Els Pauwels, Amougies (BE); Paul Van Laer, Heks (BE)

(73) Assignee: Better3fruit, N.V., Heverlee (BE)

( * ) Notice: Subject to any disclaimer, the term of this patent is extended or adjusted under 35 U.S.C. 154(b) by 4 days.

(21) Appl. No.: 13/694,825

(22) Filed: Jan. 9, 2013

(65) Prior Publication Data

US 2013/0185832 P1 Jul. 18, 2013

(30) Foreign Application Priority Data

Jan. 16, 2012 (QZ) ..... PBR 20120100

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Anne Grunberg
(74) *Attorney, Agent, or Firm* — Foley & Lardner LLP

(57) ABSTRACT

A new and distinct *Malus domestica* apple tree variety named 'Imara', particularly characterized by multiple scab resistance; powdery mildew and fire blight tolerance; smooth skin; white flesh; and slight citrus aroma.

9 Drawing Sheets

Figure 1:
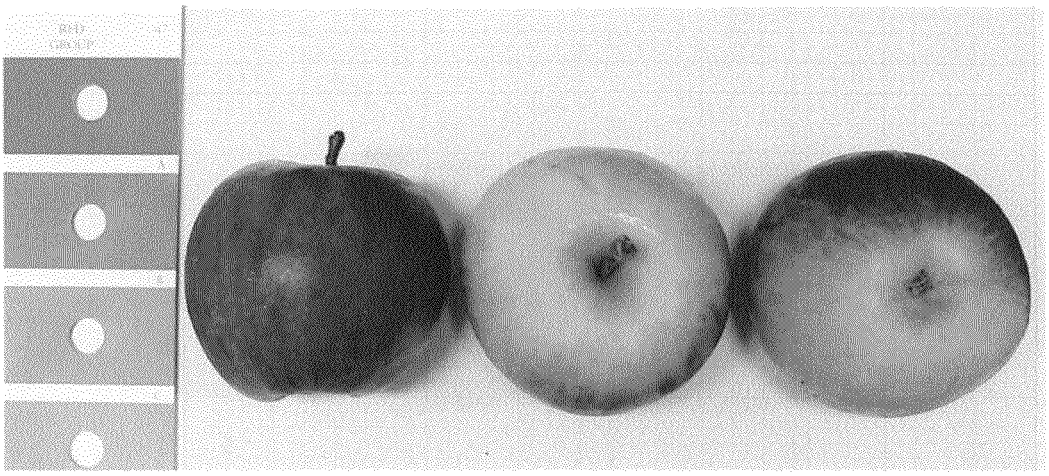

Latin name of the genus and species of the plant claimed: *Malus domestica* Borkh.

Variety denomination: 'Imara'.

PRIORITY CLAIM

This application claims priority under 35 U.S.C. §119(f) of the Community plant variety office (CPVO) application No. 2012/0100 filed Jan. 16, 2012.

BACKGROUND OF THE INVENTION

The present invention relates to a new and distinct variety of Apple tree, botanically known as *Malus domestica* Borkh. of the Rosaceae family, and hereinafter referred to by the variety denomination 'Imara'.

The new *Malus* variety is a product of a controlled breeding program conducted by the inventor(s), Inge De Wit, Hendrik Eyssen, Johan Keulemans, Johan Nicolaï, Els Pauwels and Paul Van Laer, in Rillaar, Belgium. The objective of the breeding program was to develop a new *Malus* variety with scab resistance, good taste and texture, as well as good storage capacity and shelf life.

The new *Malus* variety originated from a cross made by the inventor(s) in 1990 in Belgium. The female or seed parent is the *Malus domestica* variety designated 'LIBERTY' (unpatented). The male or pollen parent is the *Malus domestica* variety designated 'GRANNY' (unpatented). The new *Malus* variety was discovered and selected by the inventors within the progeny of the stated cross in a controlled environment in 1998 in Belgium.

Asexual reproduction of the new *Malus* variety by grafting onto rootstocks was first performed in the winter of 2008-2009 in Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'Imara' which in combination distinguish this Apple tree as a new and distinct variety:

1. multiple scab resistance;
2. powdery mildew and fire blight tolerance;
3. smooth skin;
4. white flesh; and
5. slight citrus aroma.

In comparison to the parental varieties, 'LIBERTY' and 'GRANNY', 'Imara' differs primarily in the traits listed in Table 1.

TABLE 1

Comparison with Parental Varieties

| Trait | New Variety 'Imara' | Female Parent 'LIBERTY' | Male Parent 'GRANNY' |
|---|---|---|---|
| Fruit: hue of over color | red | purple-red | none |
| Scab resistance | resistant | resistant | sensitive |
| Fruit: time for harvest | $4^{th}$ week October | $4^{th}$ week September-$1^{st}$ October | too late for Belgium; does not mature |
| Fruit: aroma | medium apple aroma with a hint of citrus | low apple aroma | low apple aroma |

Of the many commercial varieties known to the present inventor(s), the most similar in comparison to the new *Malus* variety 'Imara' is the *Malus* variety 'BRAEBURN' (unpatented), in the following characteristics described in Table 2:

TABLE 2

| Comparison with Similar Variety | | |
|---|---|---|
| Characteristic | New Variety 'Imara' | Comparison Variety 'BRAEBURN' |
| Fruit: ground color | green | yellow green |
| Fruit: color of flesh | white | cream |
| Fruit: hue of over color | red | brown red |

BRIEF DESCRIPTION OF THE PHOTOGRAPHS

The accompanying photographs illustrate the overall appearance of the new *Malus* variety 'Imara' showing the colors as true as is reasonably possible with colored reproductions of this type. Colors in the photographs may differ slightly from the color values cited in the detailed botanical description, which accurately describe the color of 'Imara'.

FIG. 1 — shows a close-up view (side, top and bottom) of mature fruit of 'Imara'.

Figure 2:
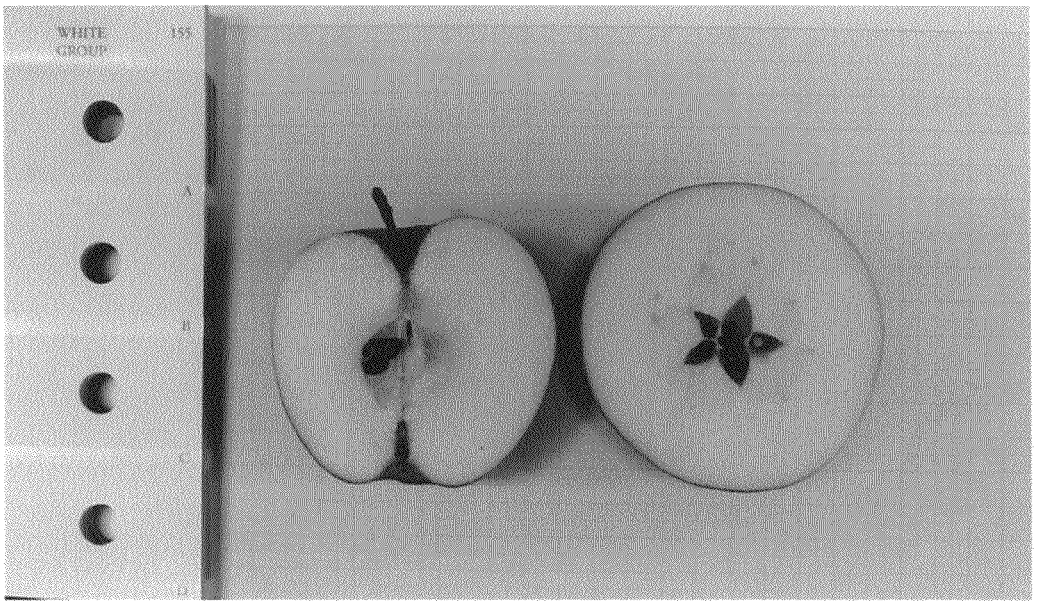

FIG. 2 — shows dissection views of mature fruit of 'Imara'.

Figure 3:
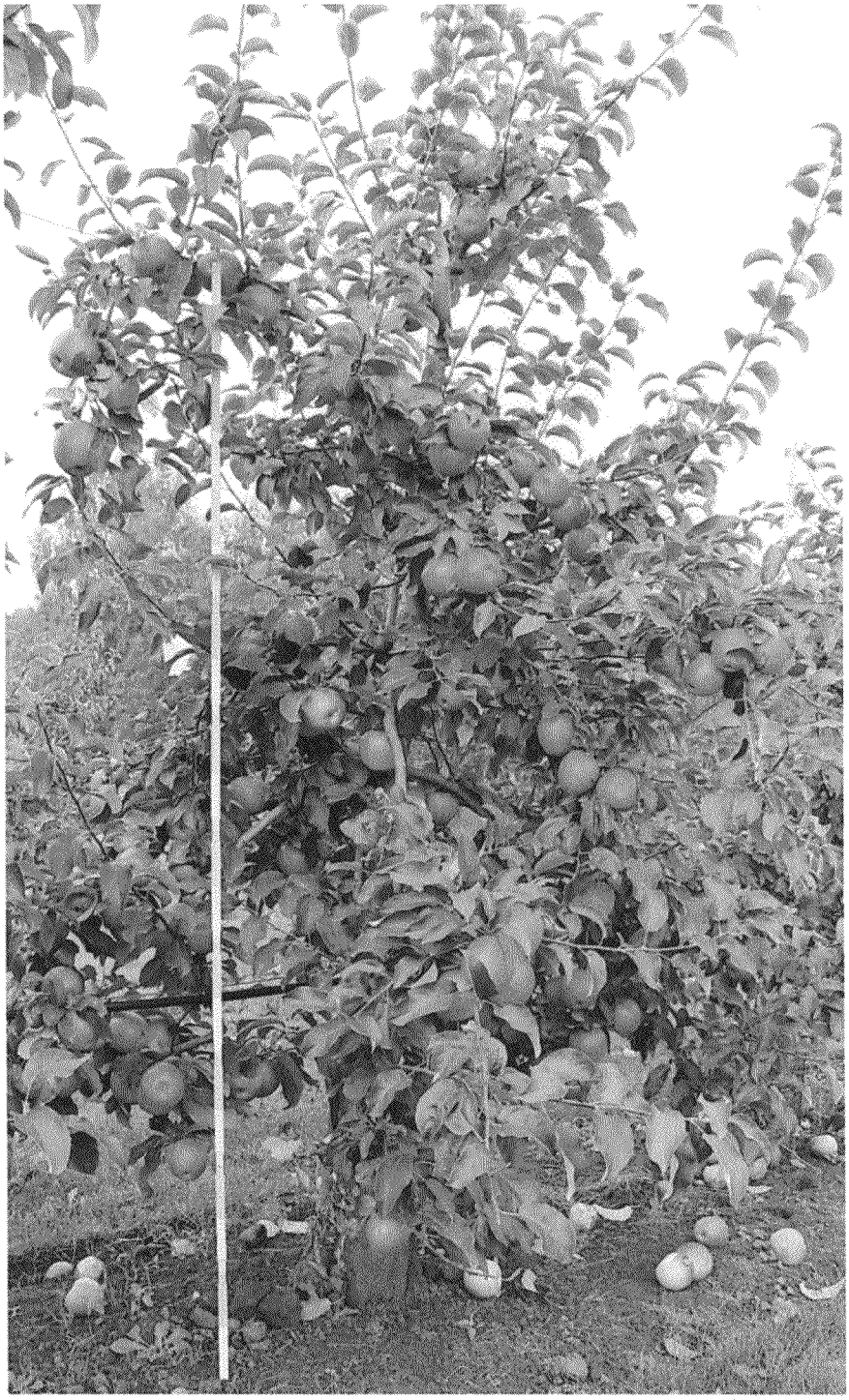

FIG. 3 — shows a fruit-bearing tree of 'Imara', at 12 years of age.

Figure 4:
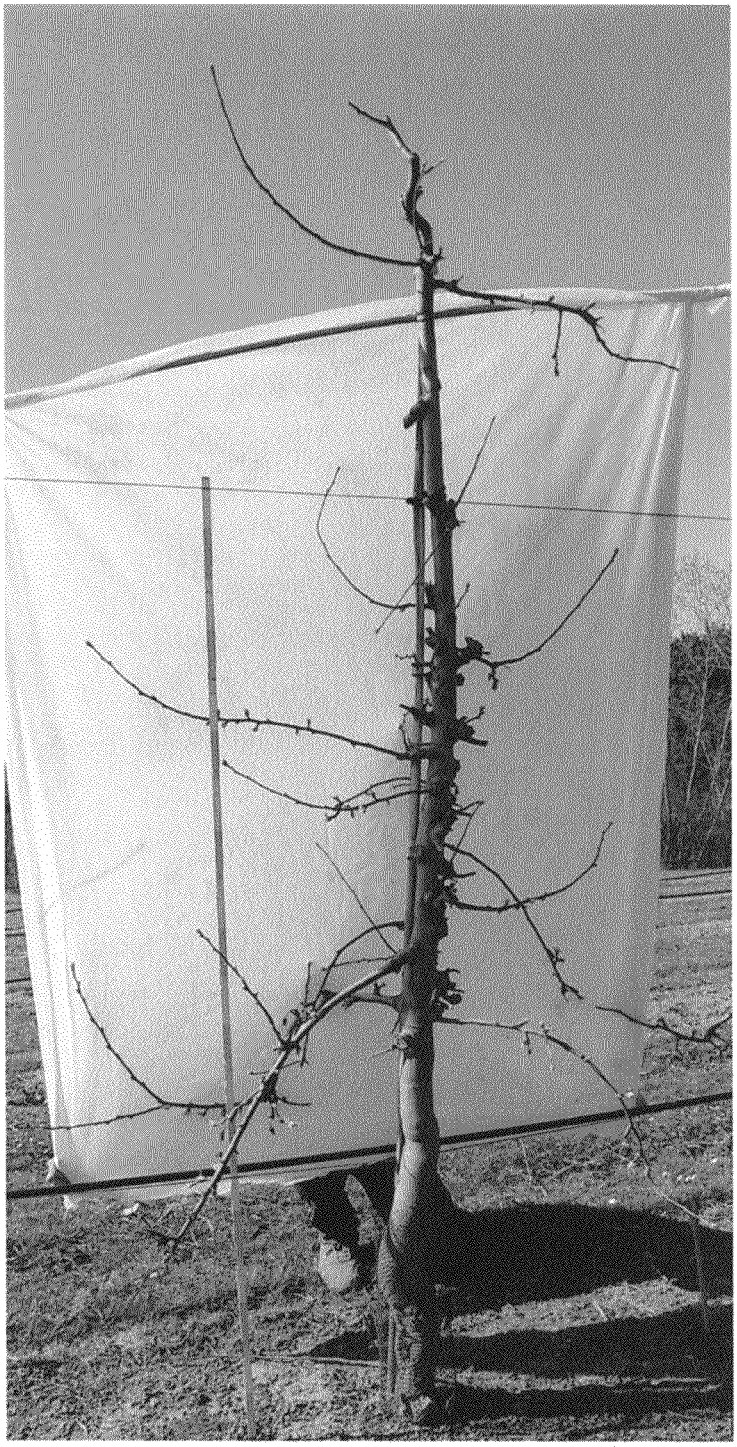

FIG. 4 — shows a dormant tree of 'Imara', at 12 years of age

Figure 5:
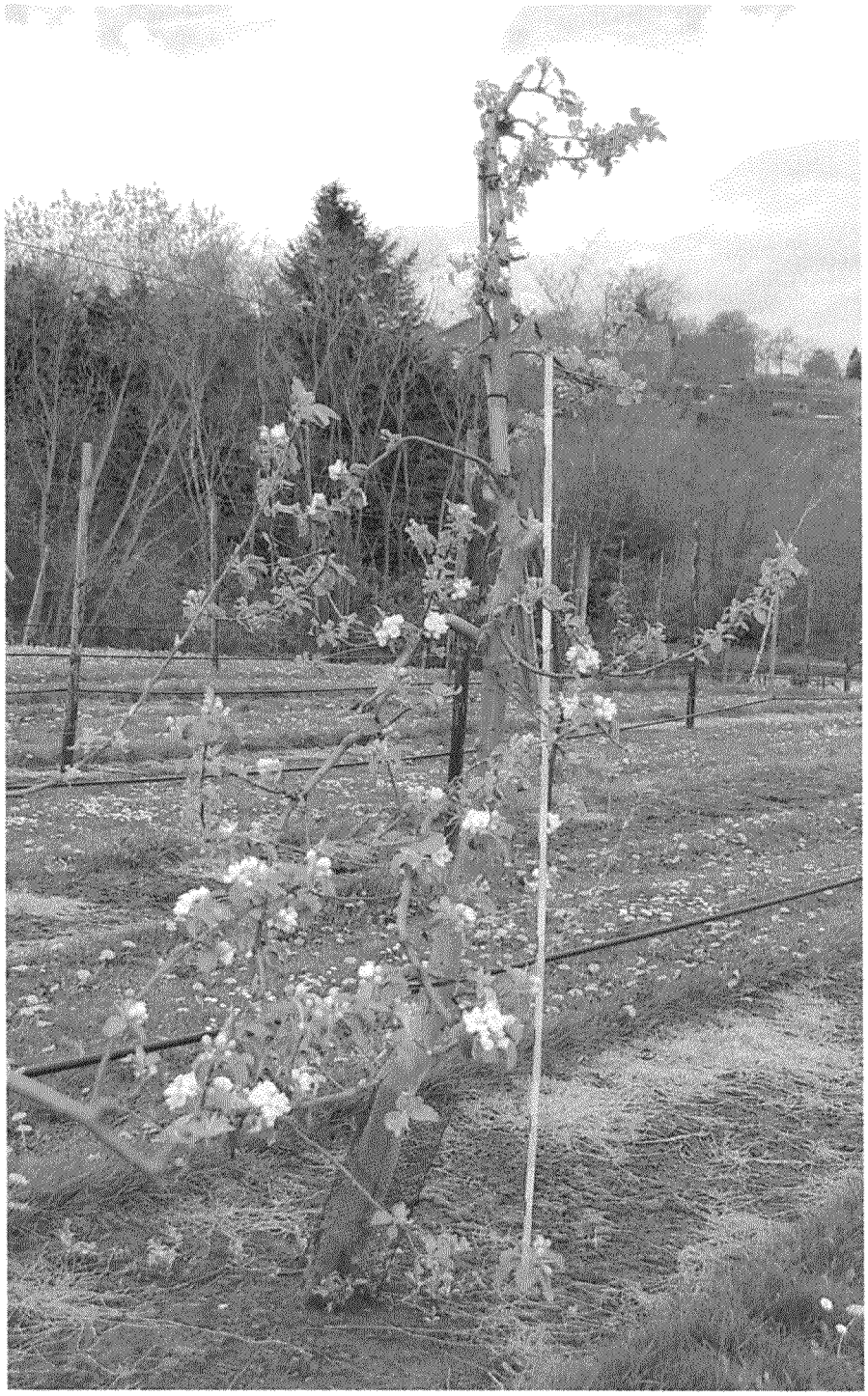

FIG. 5 — shows a blooming tree of 'Imara', at 12 years of age.

Figure 6:
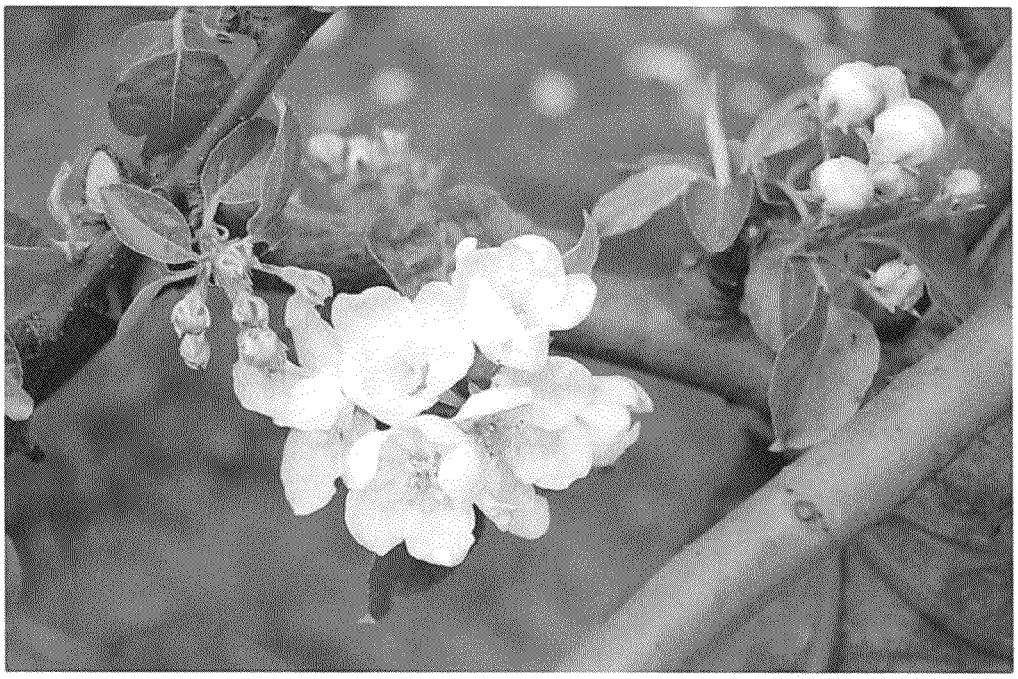

FIG. 6 — shows inflorescence of 'Imara'.

Figure 7:
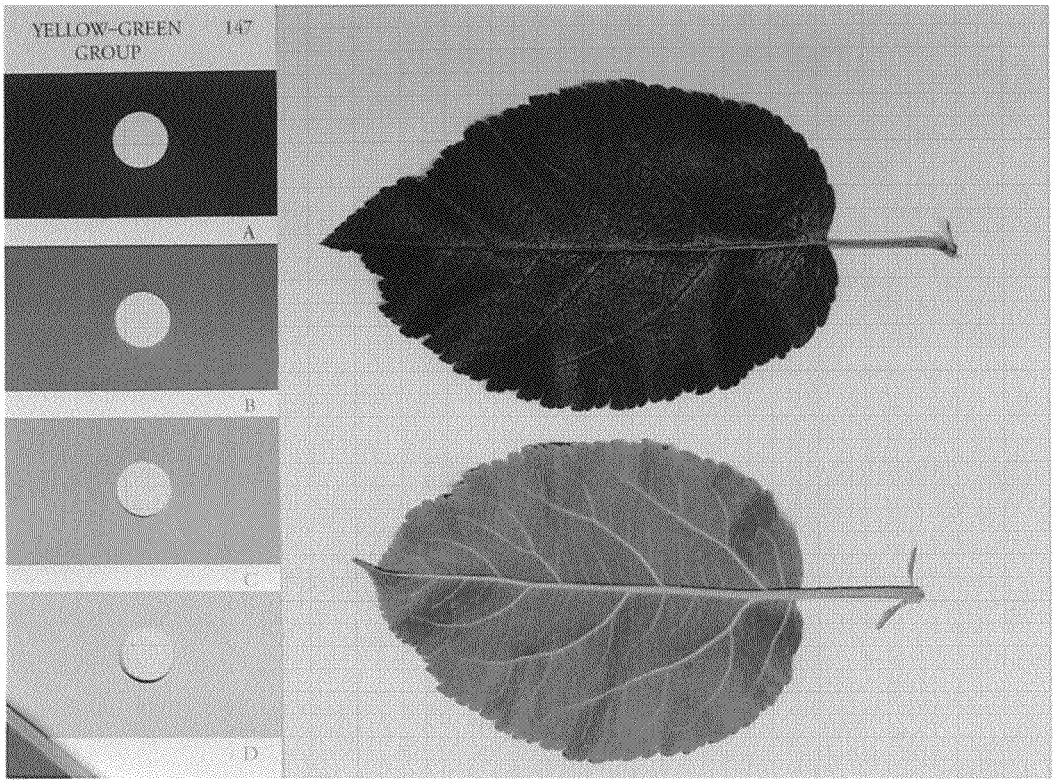

FIG. 7 — shows the upper surface (top) and under surface (bottom) view of leaves of 'Imara'.

Figure 8:
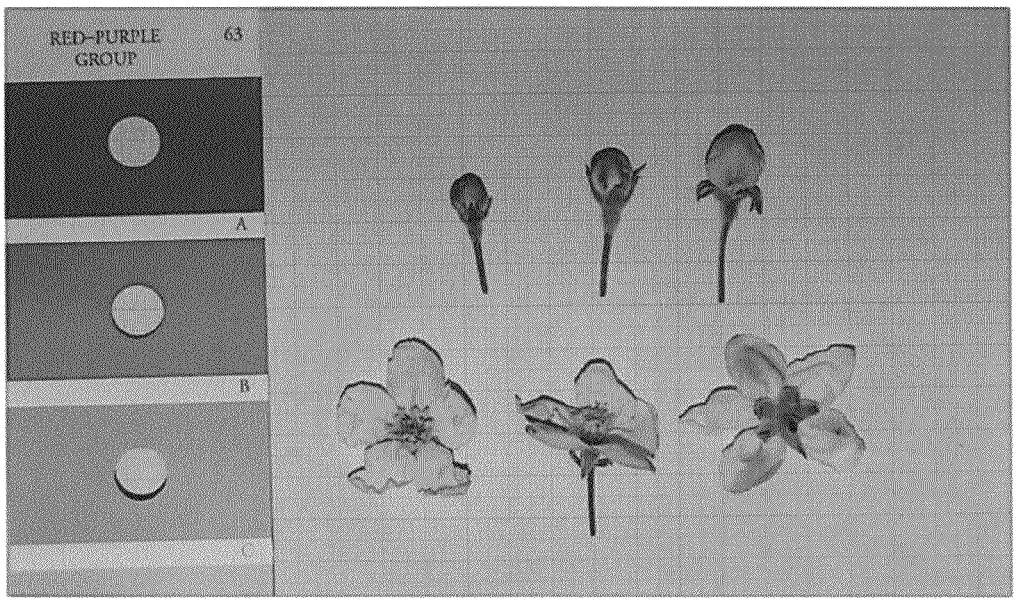

FIG. 8 — shows different stages of development of the flowers and the (from left to right) top, side and bottom view of a fully expanded flower of 'Imara'.

Figure 9:
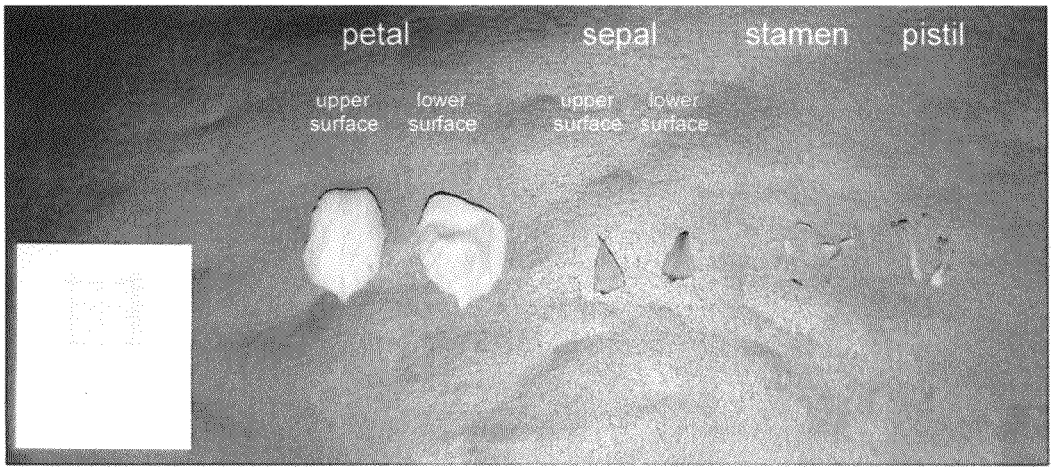

FIG. 9 — shows different parts of a flower of 'Imara'.

DETAILED BOTANICAL DESCRIPTION

The new *Malus* variety 'Imara' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'Imara' as grown in Rillaar, Belgium, under conditions which closely approximate those generally used in commercial practice.

Unless otherwise stated, the detailed botanical description includes observations, measurements and values based on 12 year old 'Imara' trees grown in Rillaar, Belgium from 2002 to 2012. Quantified measurements are expressed as an average of measurements taken from a number of trees of 'Imara'. The measurements of any individual tree, or any group of trees, of the new variety may vary from the stated average.

Color references are made to The Royal Horticultural Society Colour Chart (R.H.S.), ($4^{th}$ edition, 2001), except where general colors of ordinary significance are used. Color values were taken under daylight conditions.

All of the trees of 'Imara', insofar as they have been observed, have been identical in all the characteristics described below.

Classification:

*Botanical.*—*Malus domestica.*

Parentage:

*Female or seed parent.*—*Malus* variety designated 'LIBERTY' (unpatented).

*Male or pollen parent.*—*Malus* variety designated 'GRANNY' (unpatented).

Propagation: Grafting onto rootstocks.

Growing conditions:

*Light intensities.*—Full sunlight.

*Temperature.*—During day, grown in range of 2° C. to 23° C., and during evening, grown in range of −5° C. to 13° C. C (based on average month temperature).

Tree:

*Age.*—Observed trees were 12 years old.

*Vigor.*—Strong vigor.

*Form.*—Drooping.

*Habit.*—A medium-sized tree with one trunk and about 7+/−1 leaders; main branches spreading; crown symmetrical.

*Branching habit.*—Main branches angle is about 82+/−9° with respect to trunk if allowed to grow naturally.

*Density.*—About 2200 trees per hectare.

*Cropping behavior.*—Normal beginning production, good and constant productivity, regular flowering, no biennial bearing.

*Type of bearing.*—On spurs only.

*Production.*—About 35 kg/tree in 2011.

*Size at maturity.*—Height: About 275+/−12 cm. Spread: About 176+/−25 cm.

*Trunk.*—Height (up to leaders): About 83+/−5 cm. Diameter: About 80+/−10 mm. Texture: Slightly rough. Bark color: Primarily RHS 197C, with RHS 165B, underbark. Trunk Lenticels: Length: About 1.1+/−0.2 mm. Width: About 3.8+/−0.6 mm. Color: RHS 162B. Density: About 1.0+/−0.3 per $cm^{2.}$

*Branches.*—Number per tree: About 14+/−3. Length: Maximum of 102+/−11 cm; minimum of 2+/−1 cm. Diameter (at 2 years): About 13+/−4 mm. Surface texture: Slightly rough. Pubescence: Medium. Color: Mature (after about 3 years old): RHS N199C. New Growth: RHS 166A. Internode length: About 2.8+/−0.5 cm. Internode diameter: About 15+/−4 mm. Branch lenticels: Length: About 1.0+/−0.2 mm. Width: About 1.8+/−0.4 mm. Color: RHS 161B. Density: About 2.4+/−0.9 per $cm^{2.}$

*Spur.*—Present: Yes. Distance between each spur: On the 2 and 3 year old branches, the distance is about 3+/−1 cm. Diameter of each spur: About 6+/−2 mm. Number of fruit per spur: About 1+/−1.

Foliage:

*Arrangement.*—Alternate, simple, petiolated.

*Lamina.*—Size: Length: About 98+/−15 mm (fully expanded leaf). Width: About 62+/−9 mm (fully expanded leaf). Length/width ratio: 1.6+/−0.4. Overall Shape: Ovate, petiolated. Base shape: Rounded (obtuse). Apex shape: Acute to acuminate. Margin: Biserrate. Texture: Upper surface: Smooth, slight pubescence. Under surface: Medium pubescence. Attitude in relation to shoot: Outwards at the base of branches, upwards at the end of branches. Color (mature leaves): Upper surface: RHS 147A. Under surface: RHS 138B. Color (immature leaves): Upper surface: RHS 143A. Under surface: RHS 139C. Venation: Type: Pinnate venation from central vein to the leaf edge. Color: RHS 138C.

*Petiole*.—Length: About 29+/−6 mm. Diameter: About 1.5+/−0.2 mm. Texture: High pubescence. Color: RHS 144B (upper), RHS 139D (lower), RHS 59B (at the petiole base; upper and lower surfaces).

*Stipule*.—Arrangement: Free standing. Length (distance of stipules from basal attachment of petiole): About 8.6+/−2.5 mm. Width: About 1.1+/−0.7 mm.

Inflorescence:

*Blooming time*.—Late.

*Blooming period*.—About 1 week.

*Fragrance*.—Slight.

*Type*.—Corymb.

*Number of flowers per inflorescence*.—About 6.6+/−0.7.

*Inflorescence size*.—Diameter: About 79+/−7 mm. Depth: About 48+/−4 mm.

*Buds*.—Terminal Buds: Number per spur: About 1. Shape: Pointy, triangular. Length: About 10.1+/−1.3 mm. Width: About 5.1+/−0.3 mm. Texture: Smooth, medium pubescence. Color: Apex RHS 200A, and base RHS 177A. Scales: Number: About 6.7+/−0.9. Overall shape: Triangular, folded double around bud. Apex shape: Mucronate or 3 sharp points. Base shape: Straight, fully grown together at base. Color: Upper: RHS 177A. Lower: RHS N144C. Lateral Buds: Number per branch: Between 0 and 40. Shape: Pointy, triangular. Length: About 4.2+/−1.0 mm. Width: About 3.2+/−0.3 mm. Texture: Smooth, slight pubescence at apex. Color: Apex RHS 200A, and base RHS 144C. Scales: Number: About 5.6+/−0.8. Overall shape: Triangular, folded double around bud. Apex shape: Acuminate or 3 sharp points. Base shape: Straight, fully grown together at base. Color: Upper: RHS 200B. Lower: RHS N144C.

*Petals*.—Arrangement: Overlapping. Number per flower: 5. Size: Length: About 21+/−2 mm. Width: About 15+/−1 mm. Length/width ratio: 1.4+/−0.1. Overall shape: Ovate. Apex shape: Obtuse. Base shape: Rounded. Texture (upper surface): Smooth. Texture (lower surface): Smooth. Margin: Entire. Color (upper surface): Apex, RHS 63D, and base, RHS 69D. Color (lower surface): Apex, RHS 63C, and base, RHS 69D.

*Sepals*.—Number per flower: 5. Size: Length: About 9+/−1 mm. Width: About 4.7+/−0.6 mm. Length/width ratio: 1.9+/−0.2. Overall shape: Triangular. Apex shape: Acute. Base shape: Truncate. Texture (upper surface): Smooth, hairy. Texture (lower surface): Smooth, hairy. Margin: Entire. Color (upper surface): Apex, RHS 179B, and base, RHS 143C. Color (lower surface): Apex, RHS 179B, and base, RHS 143C.

*Pedicel*.—Length: About 23+/−3 mm. Diameter: About 1.3+/−0.1 mm. Texture: Smooth, hairy (white hairs). Color: RHS 146B.

Fruit:

*Keeping quality*.—The fruit can be stored in cold temperature conditions for minimum 5 months. It has a shelf life of minimum 1 week.

*Maturity when described*.—3 weeks after harvest.

*Maturity period after full bloom*.—About 6 months after full bloom.

*Date of first and last picking* (*harvest*).—About fourth week of October.

*Type*.—Pome.

*General shape*.—Cylindrical-globose.

*Average weight*.—About 216+/−29 g.

*Fruit size*.—Average height: About 73+/−6 mm. Average diameter (at widest point): About 79+/−3 mm. Position of maximum diameter: ½ of height. Height/thickness ratio: About 0.9+/−0.1.

*Stem*.—Length: About 18+/−3 mm. Diameter: About 2.2+/−0.3 mm. Color: RHS N167A; 152B; N144B.

*Stalk cavity*.—Depth: About 15.0+/−2.0 mm. Width: About 32.6+/−2.0 mm.

*Eye basin*.—Depth: About 9.1+/−1.6 mm. Width: About 28.8+/−2.9 mm. Crowning at calyx end: Moderate. Position of sepals: Closed. Calyx tube: Fully open.

*Skin*.—Thickness: About 0.4+/−0.1 mm. Texture: Tough. Bloom: Absent. Greasiness: Absent. Firmness (at picking time): About 7.7+/−0.5 kg/cm$^2$. Overcolor Color: RHS 47B, 47C. Percentage of skin surface with overcolor color: About 50 to 75%. Pattern of overcolor: Solid flush with weakly defined stripes. Intensity of overcolor: High, bright. Ground color: RHS 150C, 150D. Skin Lenticels: Length/width: Very small dots (edges not clearly defined). Color: RHS 145A (on ground color); 191B (on overcolor). Density: About 3.8+/−2.1 n° per cm$^2$.

*Flesh*.—Color: RHS 155B. Texture: Little juicy to juicy, firm, a little spongy. Aroma: Medium apple aroma with a hint of citrus. Eating quality: Good texture and taste. Firmness (at picking time): About 8.4+/−0.4 kg/cm$^2$. Sugar content (at picking time): About 13.9+/−0.4% Brix. Acidity/Starch (at picking time): About 6.5+/−1.1 g/l malic acid. Core: Symmetry of core: Round. Distinctness of core lines: Strong. Locules: Number (per fruit): 5. Length: About 11+/−1 mm. Width: About 6+/−1 mm. Form: Teardrop form; moderately open.

Seeds:

*Number per fruit*.—About 12.7+/−3.3.

*Number per locule*.—About 2.6+/−0.6.

*Shape*.—Teardrop form.

*Length*.—About 9.1+/−0.9 mm.

*Width*.—About 4.9+/−0.5 mm.

*Texture*.—Smooth.

*Color*.—RHS 165A, 165B.

Reproductive organs:

*Androecium*.—Stamen: Number per flower: 20. Length: About 7.7+/−1.1 mm. Anther: Length: About 2.6+/−0.2 mm. Color: RHS 5C. Filaments: Length: About 6.5+/−0.9 mm. Color: RHS 155C. Pollen: Amount: Moderate. Color: RHS 5B. Pollination Requirements: Cross pollination.

*Gynoecium*.—Pistils: Quantity: 5. Length: About 10.7+/−0.9 mm. Color: RHS 145A. Stigmas: Width: About 0.7+/−0.2 mm. Color: RHS 145A. Ovary: Length: About 4.2+/−0.6 mm. Width: About 1.6+/−0.4 mm. Color: RHS 145A.

Use: Fresh market.

Disease/pest resistance: Multiple scab resistance, it contains the Vf gene (also known as Rvi6, or the scab resistance gene derived from *Malus floribunda*) and at least 1 more unidentified gene.

Disease/pest susceptibility: Low susceptibility to mildew and fire blight.

Winter hardiness: Tolerant to temperatures down to −10° C. without observed damage to wood and buds of dormant Apple trees.

Drought/heat tolerance: Tolerant to temperatures up to 40° C., growth is limited by drought periods without irrigation.

Shipping/storage characteristics: No sensitivity to bruising; good storability under ULO-conditions for up to 5 months.

We claim:

1. A new and distinct variety of *Malus domestica* apple tree named 'Imara', as illustrated and described herein.

* * * * *